March 25, 1947. G. A. VAN ROSSEM Plant Pat. 732
ROSE PLANT
Filed Dec. 8, 1942
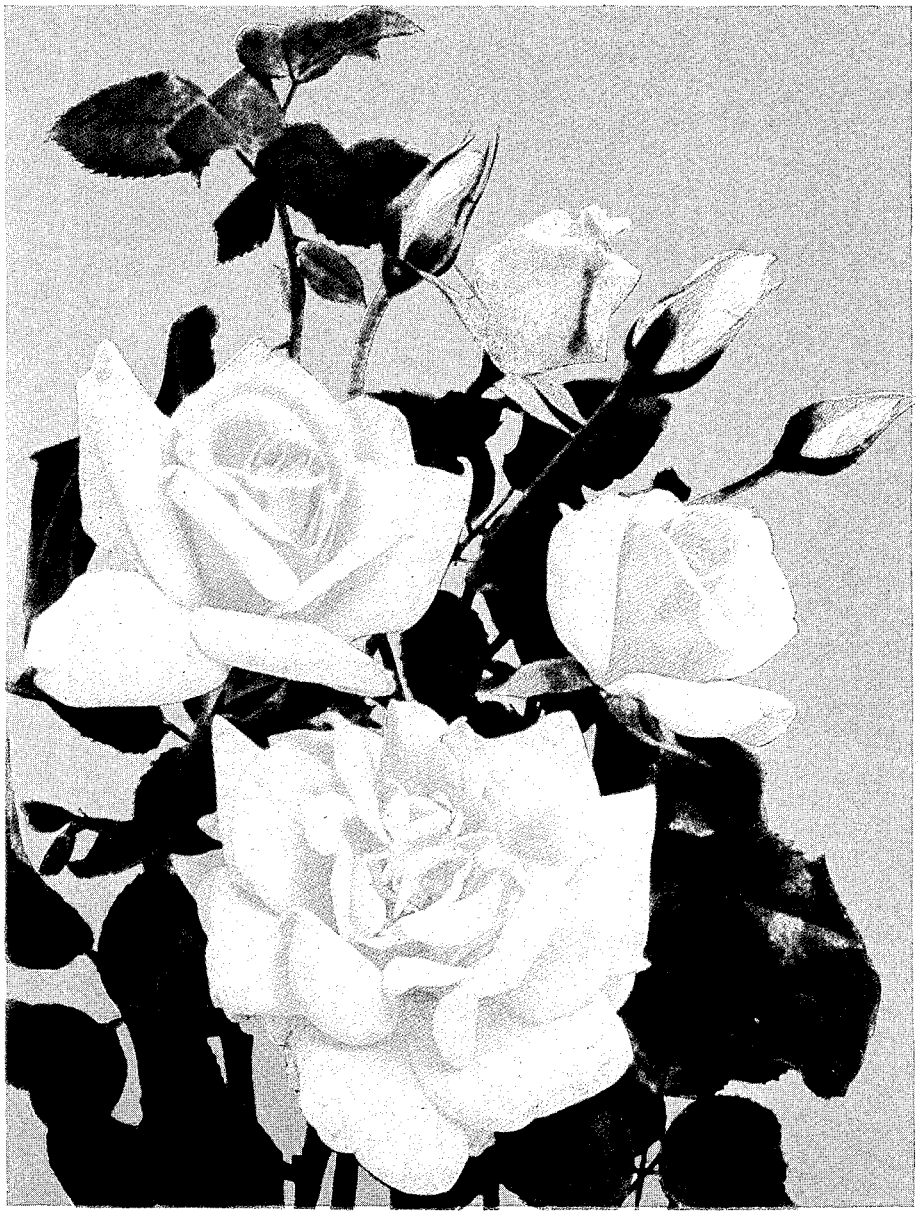
Inventor
G. A. van Rossem
By Robb & Robb
Attorneys Patented Mar. 25, 1947

Plant Pat. 732

UNITED STATES PATENT OFFICE

732

ROSE PLANT

Gerard Adriaan van Rossem, Naarden, Netherlands, assignor to Jackson & Perkins Company, Newark, N. Y., a corporation of New York Application December 8, 1942, Serial No. 468,296

1 Claim. (Cl. 47—61)

This invention relates to a new and distinct variety of hybrid tea rose plant, particularly useful for greenhouse forcing, and differing entirely in both color and growth from any previous rose of which I am aware.

This new rose is distinguished first by its tall upright growth, making very long shoots, all of which mature into flowers, and further showing greater production than the Briarcliff varieties now most commonly used.

The blooms themselves are unique, being characterized by the long pointed form of the buds, slowly unfolding into high centered flowers of novel color, changing from between Begonia Rose and Spinel Pink to between Begonia Rose and Thulite Pink as ageing occurs.

Other features of novelty will more particularly appear in the following detail description of the new rose, the color terminology being in accordance with Ridgway's Color Standard:

Parentage: Seedling.

*Seed parent.*—Unnamed seedling.

*Pollen parent.*—Unnamed seedling.

Classification: Botanic and commercial—hybrid tea.

*Flower*

(Observations made in greenhouse at Newark, New York, December 20, 1941).

Blooming habit: Recurrent—continuous.

Bud:

*Size.*—Medium.

*Form.*—Long, pointed; is not affected by wet or hot weather.

*Color.*—When sepals first divide—between Rose Red, Plate 12, and Spectrum Red, Plate 1. When petals begin to unfurl—between Rose Red, Plate 12, and Begonia Rose, Plate 1. When half blown—Inside of petals—Rose Red, Plate 1, edges of petals Begonia Rose, Plate 1, slight overcast from the base of the petal of Capucine Orange, Plate 3. Reverse of petals—Begonia Rose, Plate 1, overlaid with Capucine Orange, Plate 3, ¾ up the petal from the base.

*Sepals.*—Serrated, branched; curl back when petals begin to unfurl. Color—inside—Chrysolite Green, Plate 31; outside—Light Cress Green, Plate 31.

*Calyx.* — Shape — pear. Size — small. Aspect—smooth. Color—Light Cress Green, Plate 31.

*Peduncle.*—Length— long. Aspect — rough. Color—Yellowish Olive Green, Plate 30. Strength—bending, slender.

*Opening.*—Bud opens well; is not affected by adverse conditions.

Bloom:

*Size.*—Large; average when fully expanded, 4".

*Borne.*—Singly.

*Stems.*—Long; normal.

*Form.*—When first open—high center. Permanence—retains its form to the end.

*Petalage.*—Double (full but open center); number of petals under normal conditions, 30.

*Color.*—Center of flower—Rose Red, Plate 12. Outer petals—between Begonia Rose, Plate 1, and Thulite Pink, Plate 26, with an overcast of Orange Buff, Plate 3. Base of petals (aiglet)—Lemon Chrome, Plate 4. Inside of petals—between Begonia Rose Plate 1, and Spinel Pink, Plate 26, with an overcast of Orange Buff, Plate 3. Reverse of petals—between Begonia Rose, Plate 1, and Rose Doree, Plate 1. General tonality from a distance—Begonia Rose, Plate 1.

*Discoloration.*—General tonality at end of first day—between Begonia Rose, Plate 1, and Spinel Pink, Plate 26. Second day—between Begonia Rose, Plate 1, and Thulite Pink, Plate 26. Third day—between Begonia Rose, Plate 1, and Thulite Pink, Plate 26.

Petals:

*Texture.*—Leathery; is not affected by wet or hot weather.

*Appearance.* — Inside — shiny; outside — satiny.

*Form.*—Oval.

*Arrangement.* — Imbricated (regularly arranged shingle like). Petaloids in center—few, small.

*Persistence.*—Drop off cleanly.

*Fragrance.*—Slight. Nature—tea (average hybrid tea scent).

*Lastingness.*—On the plant and as cut flower, long.

Genital organs:

*Stamens, anthers.*—Medium size, many. Color—Deep Chrome, Plate 3. Arrangement—regular around styles.

*Stamens, filaments (threads).* — Medium length. Color—Grenadine Red, Plate 2.

*Pollen.*—Maize Yellow, Plate 4.

*Styles.*—Bunched, uneven, short, thin.

*Stigmas.*—Buff Yellow, Plate 4.

3

*Plant*

Form: Bush.
Growth: Vigorous, branching.
Foliage: 5 leaflets.
*Size.*—Very large.
*Quantity.*—Abundant.
*Color.*—New foliage—upper side—Lettuce Green, Plate 5, overcast lightly with Hay's Russett, Plate 14. Old foliage — upper side—Elm Green, Plate 17; under side—Absinthe Green, Plate 31.
*Shape.*—Oval pointed.
*Texture.*—Upper side—glossy; Under side—rough. Ribs and veins—prominent.
*Edge.*—Serrated (saw toothed).
*Serration.*—Single, large, sharp.
*Leaf stem.*—Yellowish Olive, Plate 30. Under side—prickles.
*Stipules.*—Medium length, serrated.
*Disease resistance.*—Resistant.
Wood:
*New wood.*—Color—Vandyke Red, Plate 13. Bark—smooth.
*Old wood.*—Color—Brownish Olive, Plate 30. Bark—smooth.

4

Thorns:
*Thorns.*—Quantity—on main stalks from base and on laterals from stalk—ordinary. Form—narrow base; medium length, hooked downward. Color when young—Carmine, Plate 1. Position—irregular.
*Prickles.*—Quantity—on main stalks—none.
*Short needles.*—Quantity—on main stalks and on laterals—none.

I claim:

A new and distinct variety of rose plant characterized as to novelty by its habit of tall upright growth producing very long shoots all maturing into flowers and having greater production than varieties commonly used for greenhouse forcing purposes, by the shape of its unique flower initiating in long pointed buds which unfold slowly into high centered blooms, and the peculiar color range of the blossom from the full open stage to its finish, substantially as shown and described.

GERARD ADRIAAN VAN ROSSEM.